(12) United States Patent
Brochard et al.

(10) Patent No.: US 8,269,968 B2
(45) Date of Patent: Sep. 18, 2012

(54) DEVICE FOR EVALUATING THE STATE OF WETTING OF A SURFACE, EVALUATION METHOD AND ASSOCIATED INDICATION DEVICE

(75) Inventors: Jacques Brochard, Jaunay Clan (FR); Majdi Khoudeir, Poitiers (FR)

(73) Assignees: Centre National de la Recherche Scientifique (C.N.R.S.), Paris (FR); Universite de Poitiers, Poitiers (FR)

( * ) Notice: Subject to any disclaimer, the term of this patent is extended or adjusted under 35 U.S.C. 154(b) by 623 days.

(21) Appl. No.: 12/307,765

(22) PCT Filed: Jul. 2, 2007

(86) PCT No.: PCT/FR2007/001116
§ 371 (c)(1),
(2), (4) Date: Nov. 4, 2009

(87) PCT Pub. No.: WO2008/003852
PCT Pub. Date: Jan. 10, 2008

(65) Prior Publication Data
US 2010/0045984 A1 Feb. 25, 2010

(30) Foreign Application Priority Data
Jul. 7, 2006 (FR) ..................... 06 06234

(51) Int. Cl.
*G01J 4/00* (2006.01)
(52) U.S. Cl. ........ 356/369; 356/364; 356/365; 356/366; 356/367; 356/368

(58) Field of Classification Search .......... 356/364–369; 250/225
See application file for complete search history.

(56) References Cited

U.S. PATENT DOCUMENTS

| | | | | | |
|---|---|---|---|---|---|
| 3,904,293 | A | * | 9/1975 | Gee ............................... | 356/369 |
| 4,469,442 | A | * | 9/1984 | Reich ........................... | 356/364 |
| 4,585,348 | A | * | 4/1986 | Chastang et al. ............ | 356/369 |
| 4,672,196 | A | * | 6/1987 | Canino ......................... | 250/225 |
| 5,212,535 | A | * | 5/1993 | Miyazaki et al. ............. | 356/28 |

(Continued)

FOREIGN PATENT DOCUMENTS
DE 43 00 896 4/1994
(Continued)

OTHER PUBLICATIONS

International Search Report dated Oct. 31, 2007, from corresponding PCT application.

*Primary Examiner* — Sang Nguyen
(74) *Attorney, Agent, or Firm* — Young & Thompson (57) ABSTRACT

A device (2) for evaluating the state of wetting of a surface (8) includes an emitter (4) emitting a beam (F, F1, F2) which is incident in the direction of the surface (8) and a single element (12) for receiving the beam reflected by the surface (8). The device includes: A polarization (10, 13, 14) including a first polarization zone (13) and a second polarization zone (14) designed to polarize a first part (F1) and a second part (F2) of the beam in a first and a second polarization direction; and a evaluation element (28) for calculating a polarization ratio between the polarizations of the first part of the reflected beam and the second part of the reflected beam to evaluate the state of wetting of the surface (8). Also described is an evaluation process and an associated indicator device.

12 Claims, 4 Drawing Sheets

U.S. PATENT DOCUMENTS 5,314,249 A * 5/1994 Marui et al. .................. 374/128
5,552,890 A * 9/1996 Nanna et al. .................. 356/369
5,844,682 A * 12/1998 Kiyomoto et al. ......... 356/237.1

FOREIGN PATENT DOCUMENTS

| | | |
|---|---|---|
| EP | 1 207 370 | 5/2002 |
| JP | 60-15532 | 1/1985 |
| JP | 10-206314 | 8/1998 |
| JP | 2004-301708 | 10/2004 |
| JP | 2005-43240 | 2/2005 |
| JP | 2006-58122 | 3/2006 |

* cited by examiner

DEVICE FOR EVALUATING THE STATE OF WETTING OF A SURFACE, EVALUATION METHOD AND ASSOCIATED INDICATION DEVICE

BACKGROUND OF THE INVENTION

1. Field of the Invention

This invention relates to a device for evaluating the state of wetting of a surface, of a type comprising at least one emitter capable of emitting at least one light beam which is incident in the direction of the surface, the surface being able to reflect the said beam at least in part, and a single means for receiving the beam reflected from the said surface.

2. Description of the Related Art

Devices for evaluating the state of wetting of a surface based on the specific absorption properties of water for radiation in the near infrared are known. However, these devices are unsuitable for slight or very slight degrees of wetting.

SUMMARY OF THE INVENTION

The invention relates to an alternative device for evaluating the state of wetting of a surface.

With this object the invention relates to an evaluation device of the aforesaid type comprising:

polarisation means comprising at least a first polarisation zone and a second polarisation zone polarising a first part and a second part of the beam according to a first and a second polarisation direction respectively, and calculation means for calculating a polarisation ratio between the polarisations of the first part of the reflected beam and the second part of the reflected beam to evaluate the state of wetting of the surface.

According to particular embodiments the evaluation device comprises one or more of the following features:

the first polarisation zone is able to polarise only the first part of the beam and the second polarisation zone is able to polarise only the second part of the beam, the angle of incidence of the incident beam is substantially equal to the angle of reflection of the reflected beam, the angle of incidence and the angle of reflection being defined in relation to the normal to the mean plane of the surface being evaluated, the receiving means comprise a first portion receiving the first part of the beam and a second portion receiving the second part of the beam, and the size of the first receiving portion is substantially equal to the size of the second receiving portion, the first polarisation direction is substantially perpendicular to the second polarisation direction, the emitter is able to emit white light and the polarisation means are located between the surface under analysis and the receiving means, the receiving means comprise means for creating an image, the said image comprising at least a first portion and a second portion representing the first and second parts of the polarised beam respectively, and the polarisation ratio is calculated from the means of the grey levels of the first and second portions of the image, the first and second parts of the beam have a first and a second wavelength respectively, the second wavelength being different from the first wavelength, and the polarisation means are located between the emitter and the surface under analysis, and the receiving means comprise means for creating a colour image, the said image comprising pixels of a first colour capable of being excited by the first part of the beam and pixels of a second colour capable of being excited by the second part of the beam, and the polarisation ratio is calculated from the mean of the grey levels of the pixels of the first colour and the mean of the grey levels of the pixels of the second colour.

The invention also relates to a method for evaluating the state of wetting of a surface which is capable of reflecting at least a part of an incident light beam, comprising the following stages:

emission by an emitter of at least one beam incident in the direction of the surface requiring evaluation, polarisation of at least a first and a second part of the beam in a first and second polarisation direction by at least a first polarisation zone and a second polarisation zone respectively, receipt of the first and second parts of the polarised beam by receiving means, and evaluation of the state of wetting of the surface by calculating a polarisation ratio between the polarisation of the first part of the reflected beam and the second part of the reflected beam through calculation means.

According to particular embodiments, the evaluation process comprises one or more of the following features:

the receiving stage comprises a stage of creating an image representing the first and second parts of the polarised beam, and the evaluation stage comprises the following stages:

determining the wetting density of the surface by calculating the degree of saturation of the image, comparing the wetting density with at least one predetermined primary wetting density threshold, if the wetting density is below the primary wetting density threshold, comparing the polarisation ratio with a predetermined polarisation threshold, and classifying the surface as a dry surface when the polarisation coefficient is above the polarisation threshold and as a wet surface when the polarisation coefficient is below the polarisation threshold, the evaluation stage also comprises the following stages:

if the wetting density is above the primary wetting density threshold, the wetting density is compared with at least one secondary wetting density threshold, and the surface is classified as a slightly wetted surface when the wetting density is below the secondary wetting density threshold and as a heavily wetted surface when the wetting density is above the secondary wetting density threshold.

The invention also relates to a device indicating the state of wetting of a road for a motor vehicle travelling on that road, the vehicle incorporating emission/receiving means, comprising:

control means comprising:

means for connection to the vehicle's emission/receiving means to transmit a request for characterisation of the road type to a remote server, and to receive the said type, a mapping defining polarisation threshold values, of primary wetting density thresholds and secondary wetting density thresholds in relation to different road types, means for selecting at least one of the said values from the mapping on the basis of the road type received by the emission/receiving means, and means for transmitting the selected value or each selected value to an evaluation device, a device for evaluating the state of wetting on the basis of the characteristics mentioned above comprising a predetermined polarisation threshold, a predetermined primary wetting density threshold and a predetermined secondary wetting density threshold, the device being capable of receiving the value or each value selected by the control means and of modifying the predetermined value or each predetermined value by the value or each value received.

BRIEF DESCRIPTION OF THE DRAWING FIGURES

Other advantages and characteristics of the present invention will become clear from the following detailed description which is given with reference to the appended drawings which are provided purely by way of non-limiting example and in which.

DETAILED DESCRIPTION OF THE INVENTION

Figure 1:
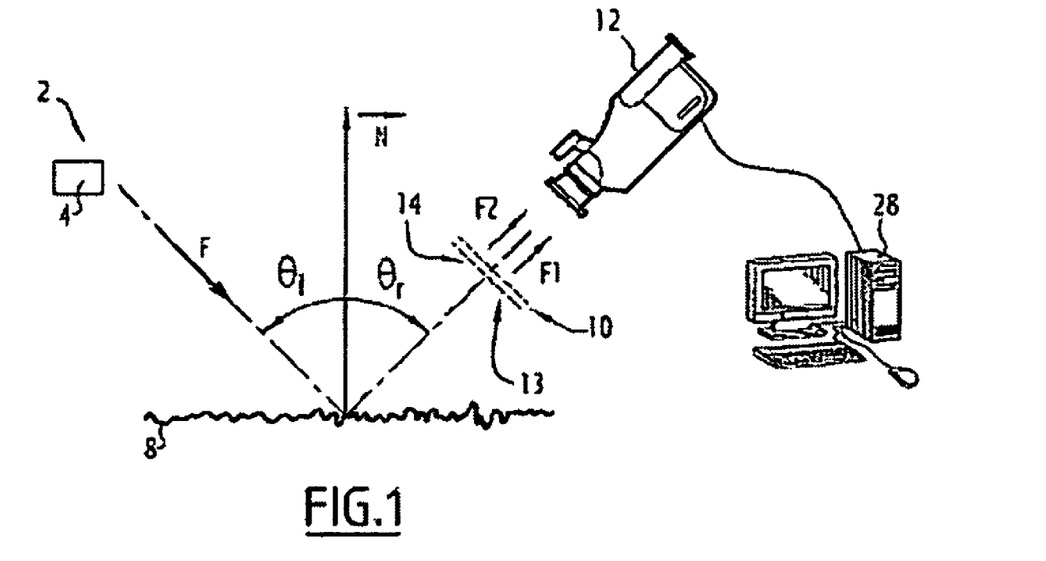
FIG. 1 is a diagrammatical view of an evaluation device according to a first embodiment of the invention.

Evaluation device 2 according to a first embodiment of the invention is illustrated diagrammatically in FIG. 1.

This comprises an emitter 4 capable of emitting a light beam F in the direction of a surface 8 of which the state of wetting is to be estimated, a polariser 10 capable of polarising the light beam F reflected by surface 8 and a camera 12 receiving the beam polarised by polariser 10.

Emitter 4 comprises for example an electroluminescent diode capable of emitting a beam F of natural white light of predetermined luminance.

Emitter 4 and camera 12 are located and fixed in relation to surface 8 in such a way that the angle of incidence $\Theta_I$ of beam F is substantially equal to the angle of reflection $\Theta_R$ of reflected beam F; angles $\Theta_I$ and $\Theta_R$ being defined in relation to a normal N to the mean plane of surface 8. Thus beam F undergoes specular reflection.

Preferably, the angle of incidence $\Theta_I$ and the angle of reflection $\Theta_R$ are equal to 30°.

Surface 8 under analysis is a rough surface capable of reflecting at least a part of beam F.

Polariser 10 has a zone 13 for linear polarisation in a first direction A and a zone 14 for linear polarisation in a second direction B perpendicular to first direction A.

Polariser 10 is located between surface 8 and camera 12 along the path of beam F so as to separate it into a first part of the beam, F1, polarised only by polarisation zone 13, and a second part of beam, F2, which is different from the first part of beam F1 and is only polarised by polarisation zone 14.

In particular, polariser 10 is fixed in the path of reflected beam F in such a way that part F1 of the beam is substantially equal to part F2 of the beam.

Polariser 10 is for example mounted on the objective of camera 12.

Camera 12 is a colour or black-and-white camera of the CCD type. It is capable of creating a digital image 15 of beam F reflected by surface 8 and polarised by polariser 10.

The optics and resolution of camera 12, and the distance between the camera and surface 8, are determined in relation to the degree of roughness of surface 8.

Camera 12 is fixed in relation to polariser 10 in such a way that its objective can receive part of beam F1 over half its aperture and part of beam F2 in the other part of its aperture.

Figure 2:
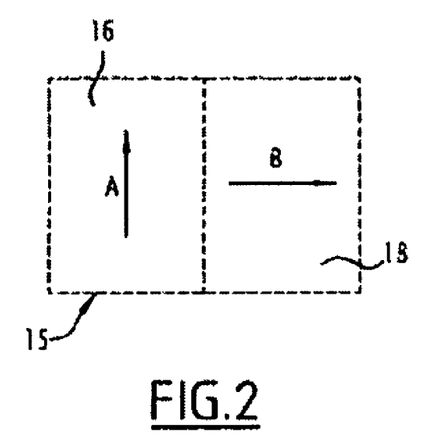
FIG. 2 is a diagrammatical front view of an image obtained by the evaluation device according to the invention.

As polariser 10 comprises a zone of polarisation in direction A and a zone of polarisation in direction B, image 15 generated by camera 12 comprises a portion 16 corresponding to the F1 part of beam F which passed through polarisation zone 13 in direction A and a portion 18 corresponding to the F2 part of reflected beam F which passed through polarisation zone 14 in direction B, as may be seen in FIG. 2.

The surface area of portion 16 of the image is equal to the surface area of portion 18 of the image because camera 12 is centred on the axis of separation between zones 13 and 14.

Evaluation device 2 also comprises a computer 28 connected to camera 12.

Computer 28 comprises calculation means, a man/machine interface of the keyboard or mouse type, and a display screen. It is capable of processing the images generated by the camera using the evaluation process described below.

Figure 3:
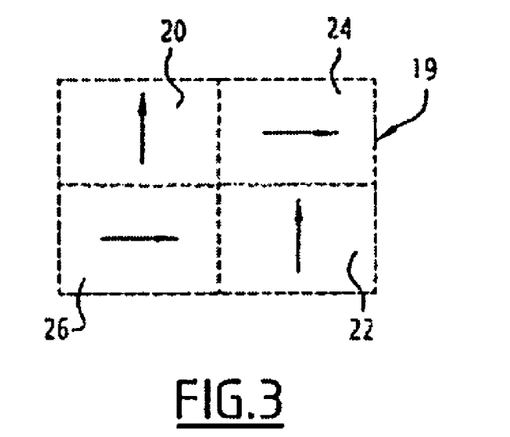
FIG. 3 is a diagrammatical front view of an image obtained by a variant of the evaluation device according to the invention.

As a variant, polariser 10 has two zones for polarisation in direction A and two zones for polarisation in direction B.

In this case the polarisation zones having the same direction of polarisation are arranged diagonally in order to obtain a more uniform distribution of each polarised zone in a given direction. Image 19 created by camera 12 comprises four portions 20, 22, 24 and 26 corresponding to the four zones of the polariser, as may be seen in FIG. 3.

As a variant, camera 12 is replaced by digital photography equipment or by a photoreceptor associated with means for determining the polarised light energy in each polarisation direction.

Figure 4:
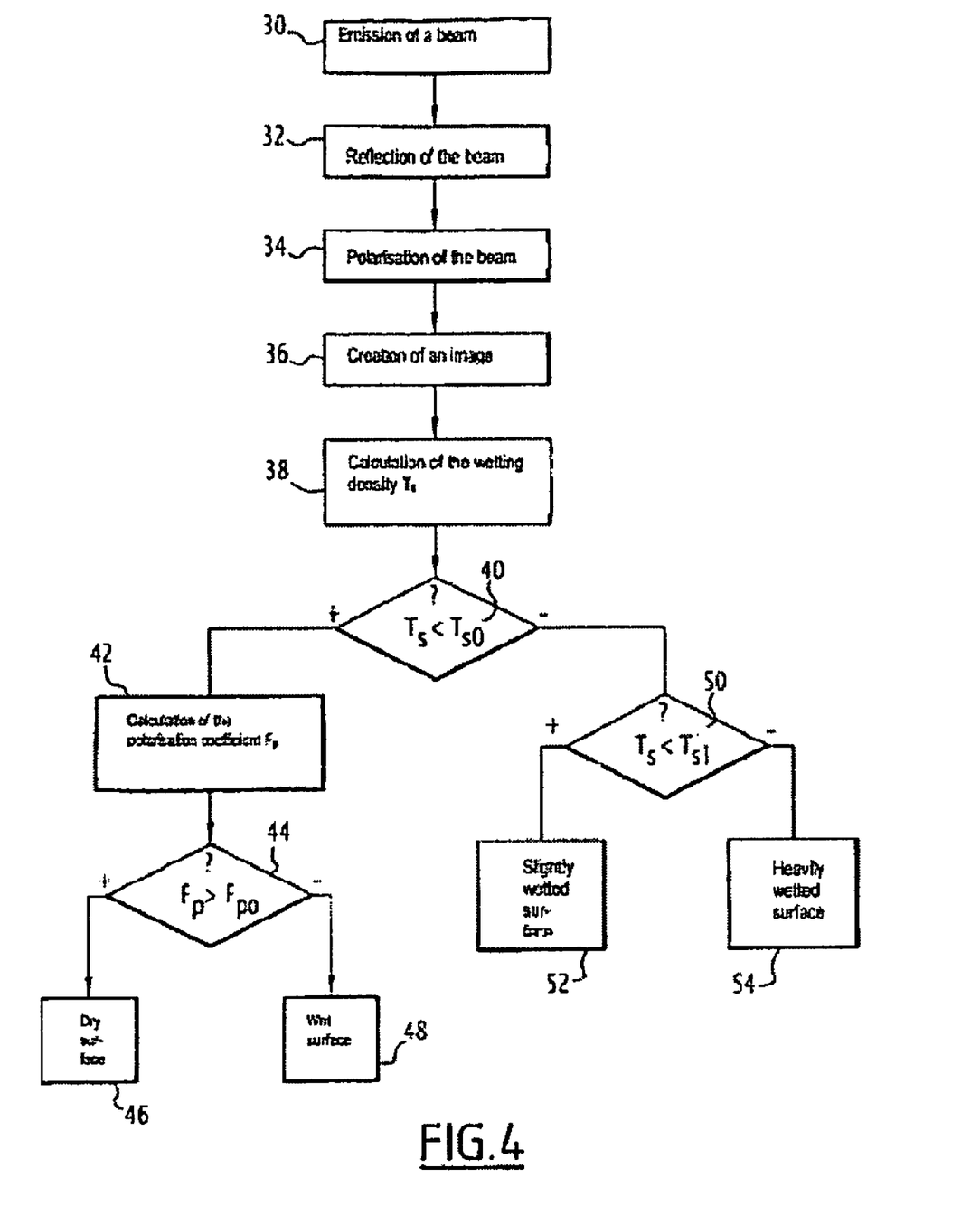
FIG. 4 is a diagram representing the stages in the evaluation process according to the invention.

As may be seen in FIG. 4, the method for evaluating the state of wetting of a surface according to the first embodiment begins with a stage 30 of the emission of a beam F by emitter 4.

In stage 32 the emitted beam F is reflected by surface 8 under evaluation.

In stage 34 beam F reflected by surface 8 passes through polariser 10. In particular part F1 of beam F passes through zone 13 of the polariser and part F2 of beam F passes through zone 14 of polariser 10.

During a stage 36 camera 12 takes a digital image of surface 8 and transmits this image to computer 28.

During stage 38 computer 28 calculates the wetting density of image 15 using the following formula:

$$T_S = 100 \times \frac{N_A}{N_T} \quad (1)$$

in which:

$T_S$ is the degree of saturation of the pixels, $N_A$ is the number of pixels having a grey level higher than threshold S, and $N_T$ the total number of pixels in image 15.

In accordance with the invention, threshold S corresponds to a grey level of more than approximately 80% of a white level.

Degree of saturation $T_S$ represents the wetting density of surface 8. When the angle of incidence $\Theta_I$ is equal to the angle of reflection $\Theta_R$, wetted surfaces have a high degree of saturation $T_S$.

In stage 40, computer 28 compares wetting density $T_S$ with a primary wetting density threshold $T_{S0}$ previously defined in the course of a calibration stage. Primary wetting density threshold $T_{S0}$ depends on surface 8 and on the luminance of the beam emitted by emitter 4.

When wetting density $T_S$ is below wetting density threshold $T_{S0}$ computer 28 calculates the polarisation coefficient $F_P$ of image 15, also known as the polarisation ratio $F_P$, in the course of a stage 42.

Polarisation coefficient $F_P$ is determined on the basis of measurement of the mean energy flux received by camera 12 in each polarisation direction based on the relationship:

$$F_P = E_A/E_B \qquad (2)$$

in which:
- $E_A$ is the mean energy flux of part F1 of the beam which passed through zone 13 and is polarised in direction A,
- $E_B$ is the mean energy flux of part F2 of the beam which passed through zone 14 of polariser 10 and is polarised in direction B.

In practice, computer 28 calculates the mean of the grey levels for the pixels in portion 16 to obtain a quantity proportional to the mean energy flux $E_A$ polarised in direction A and the mean for the grey levels of portion 18 of image 15 to obtain a quantity proportional to the mean energy flux $E_B$ polarised in direction B.

During a stage 44 computer 28 compares polarisation coefficient $F_P$ with a previously defined polarisation threshold $F_{P0}$. Polarisation threshold $F_{P0}$ is for example approximately equal to 1.

In an embodiment such that polarisation threshold $F_P$ decreases as the degree of wetting increases, computer 28 indicates on its screen that surface 8 under evaluation is dry, in the course of a stage 46, if polarisation coefficient $F_P$ is above polarisation threshold $F_{P0}$.

When polarisation coefficient $F_P$ is below polarisation threshold $F_{P0}$, the computer displays that surface 8 is wet, in the course of stage 48.

When in the course of stage 40 wetting density $T_S$ is above primary wetting density threshold $T_{S0}$ the computer compares wetting density $T_S$ with secondary wetting density threshold $T_{S1}$ in the course of a stage 50.

When wetting density $T_S$ is below wetting density threshold $T_{S1}$ computer 28 displays on its screen that surface 8 is slightly wet, in the course of a stage 52.

When wetting density $T_S$ is above secondary wetting density $T_{S1}$, computer 28 displays on its screen that surface 8 is heavily wetted, in the course of a stage 54.

As a variant, the method according to the invention determines a level of confidence in the evaluation of the degree to which the surface is wetted.

For this purpose the method comprises a stage of calculating wetting density $T_S$ in each zone 16, 18 of image 14 and a stage of comparing the wetting density calculated in part 16 of image 14 with the wetting density calculated in part 18 of image 14.

When the difference between these wetting densities is below a predetermined value the camera has filmed a surface 8 which is uniformly rough or wetted. Computer 28 then displays an indicator characteristic of a satisfactory level of confidence in evaluation of the degree of wetting.

When the difference between these wetting densities is higher than a predetermined value the camera has filmed a surface 8 which is not uniformly rough or wetted. Computer 28 displays an indicator characteristic of a poor level of confidence in evaluation of the degree of wetting.

Figure 5:
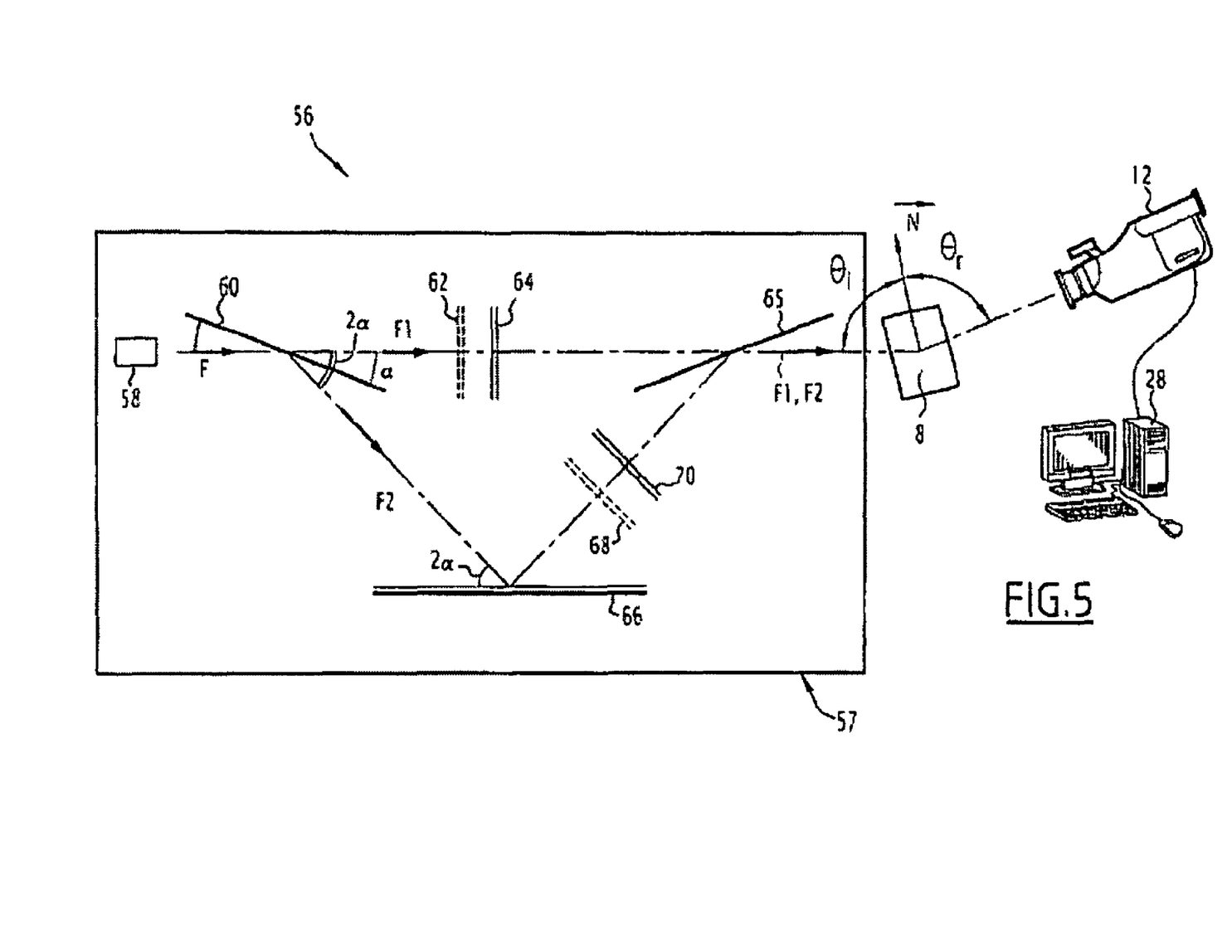
FIG. 5 is a diagrammatical view of the evaluation device according to a second embodiment of the invention.

Evaluation device 56 according to a second embodiment of the invention is illustrated diagrammatically in FIG. 5.

Elements which are identical to the elements of evaluation device 2 according to the first embodiment are indicated by the same reference numbers and will not be described again.

In this second embodiment, evaluation device 56 comprises an emitter 57 which is capable of emitting two beams towards surface 8, a camera 12 for receiving beams F1, F2 and a computer 28 connected to camera 12.

Emitter 57 is capable of emitting a first beam F1 linearly polarised in direction A having a wavelength in the vicinity of $\lambda_1$ and a second beam F2 linearly polarised in direction B having a wavelength in the vicinity of $\lambda_2$.

For this purpose emitter 57 comprises an electroluminescent diode 58, a first semi-reflecting thin sheet 60 and a collimation device, which is not shown, mounted between electroluminescent diode 58 and thin sheet 50.

Electroluminescent diode 58 is capable of emitting a beam of white light F.

First thin sheet 60 is located along the path of beam F. It forms an angle $\alpha$ with beam F. It is capable of splitting the beam into a first beam F1 which passes through thin sheet 60 and a second beam F2 which is diverted therefrom through an angle of $2\alpha$.

Emitter 57 also comprises a polariser 62 and a separator filter 64 located on the path of first beam F1 and a second semi-reflecting thin sheet 65 located on the optical path of first beam F1 and second beam F2 in such a way that its main surface makes an angle $\alpha$ with the first and second beams.

Polariser 62 has a single polarisation zone polarising first beam F1 in direction A.

Filter 64 is capable of filtering out waves of wavelength other than wavelength $\lambda_1$. Wavelength $\lambda_1$ is close to 550 nm and corresponds to a beam of a green colour.

First beam F1 passes through a semi-reflecting sheet 65. Second beam F2 is diverted by semi-reflecting sheet 65.

Emitter 57 also comprises a mirror with silvered surfaces 66, a polariser 68 and a separating filter 70 located between mirror 66 and semi-reflecting thin sheet 65.

Mirror 66 is positioned in the path of second beam F2. Its main surface makes an angle of $2\alpha$ with respect to second beam F2, so that the second beam is reflected towards semi-reflecting sheet 65. Angle $\alpha$ is for example close to 10° when the sheets are ordinary parallel-sided sheets of glass.

Polariser 68 has a single polarisation zone polarising the beam in a direction B perpendicular to polarisation direction A.

Filter 70 is capable of filtering out rays of wavelength other than wavelength $\lambda_2$. Wavelength $\lambda_2$ is close to 650 nm and corresponds to a beam of a red colour.

Camera 12 is a colour camera.

Camera 12 is fixed in relation to emitter 57 in such a way that the angle of incidence $\Theta_I$ of beam F is equal to the angle of reflection $\Theta_R$ Of reflected beam F. The angles of incidence and reflection are measured in relation to the normal N to the mean plane of surface 8.

According to the second embodiment the image obtained comprises two colours, one of which corresponds to the pixels of green colour excited by first beam F1 of wavelength $\lambda_1$ polarised in direction A and the other to pixels of red colour excited by second beam F2 of wavelength $\lambda_2$ polarised in direction B. The pixels of red and green colour are distributed over the entire image.

Computer 28 is capable of carrying out the method of evaluation as described previously and illustrated in FIG. 4.

In particular, computer 28 is capable of calculating wetting density $T_S$ from the formula stated at (1) in which $N_A$ is the number of pixels having a grey level above threshold S, regardless of the colour of the pixels.

In order to calculate polarisation coefficient $F_P$, computer 28 is capable of calculating the mean of the grey levels of the pixels of red colour in order to obtain the mean energy flux $E_A$ of beam F1 polarised in direction A and the mean of the grey levels of the pixels of green colour to obtain the mean energy flux $E_B$ of beam F2 polarised in direction B.

For this purpose computer 28 is capable of distinguishing the grey levels of an image and its chrominance at the same time.

In order to calculate the level of confidence when evaluating the state of wetting using evaluation device 56 according to the second embodiment, computer 28 can calculate wetting density $T_S$ only for the pixels of a given colour and wetting density $T_S$ only for the pixels of the other colour, and compare these two wetting densities.

As a variant, filters 70 and 64 have colours other than the colours green and red.

As a variant, thin sheet 60 is replaced by the use of a second electroluminescent diode which is capable of emitting white light.

As a variant, green filter 70 and red filter 64 and diode 58 are replaced by two electroluminescent diodes which are capable of emitting green light and red light.

Figure 6:
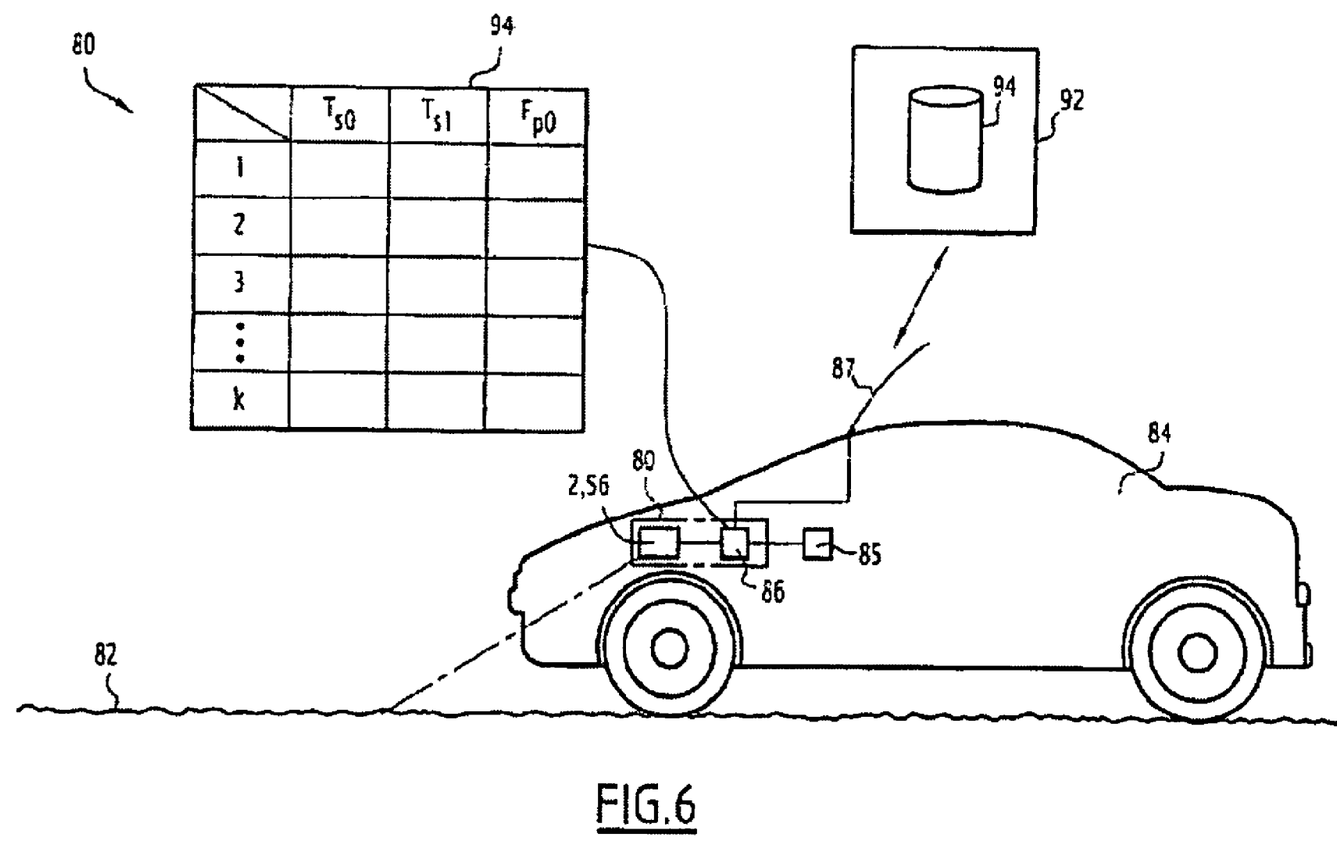
FIG. 6 is a diagrammatical view of a device indicating the state of wetting of a road for a motor vehicle.

Device 80 indicating the state of wetting of a road 82 is illustrated diagrammatically in FIG. 6.

It is intended to be mounted on a motor vehicle 84 travelling on a road 82 and incorporating a navigation device 85 and emission/receiving means 87.

Indicator device 80 comprises an evaluation device 2, 56, control means 86 connected to evaluation device 2, 56, navigation device 85 and emission/receiving means 87.

Evaluation device 2, 56 is identical to the evaluation device according to the first or second embodiments of the invention.

The optics and resolution of the camera and the distance between it and the road are selected so that the evaluation device is able to detect the state of wetting of a road 82 having irregularities of between a few millimeters and a few centimeters.

Evaluation device 2, 56 is capable of receiving a polarisation threshold $F_{P0}$, a primary wetting density threshold $T_{S0}$ and a secondary wetting density threshold $T_{S1}$ at a predetermined frequency from control means 56 and of altering the values of the predetermined parameters in its process whenever new values are received.

In a manner which is in itself known, navigation system 85 can communicate with a remote server, not shown, to receive the geographical position of vehicle 84.

On receipt of this location information control means 86 can transmit a request for the characterisation of road type 82 to a remote server 92. The characterisation request includes the geographical position of vehicle 84 and as a consequence the geographical position of road 82.

Remote server 92 includes a database 94 which can store information on the location of the road and the road type in relation to location. For example roads may be classified into different families according to the date of their construction, their composition or their roughness.

Server 92 is designed to transmit the road type to control means 86 through receiving means 87.

Control means 86 are designed to receive the road type transmitted by server 92.

Control means 86 incorporate mapping 94 which will define a polarisation threshold $F_{P0}$, a primary wetting density threshold $T_{S0}$ and a secondary wetting density threshold $T_{S1}$ for each type of road. The values of polarisation threshold $F_{P0}$, primary wetting density threshold $T_{S0}$ and secondary wetting density threshold $T_{S1}$ from mapping 94 will have all been previously established for each road type in the course of a learning stage.

Control means 86 are able to select polarisation threshold $F_{P0}$, primary wetting density threshold $T_{S0}$ and secondary wetting density threshold $T_{S1}$ from mapping 94 on the basis of the type of road received by emission/receiving means 87.

Control means 86 are able to transmit these values to evaluation device 2, 56 at a previously established frequency.

Evaluation device 2, 56 is designed to take the values received from control means 86 as predetermined values for implementing the method illustrated in FIG. 4.

As a variant, sheets 60, 65 are semi-reflecting and angle α is 45°.

Advantageously this variant will provide better light efficiency from the light sources.

Advantageously, measuring polarisation coefficient $F_P$ will make it possible to distinguish dry roads from wet roads. In fact a surface is regarded as comprising a set of micro-facets and when the angle of incidence $\Theta_I$ is equal to the angle of reflection $\Theta_R$, each micro-facet shows specular photometric behaviour when it is covered with water and diffuse photometric behaviour when it is not covered with water.

Advantageously the evaluation device according to the invention comprises a single reception means so that the device is free from parallax problems, i.e. there is no need to position each camera receiving a light beam precisely in order to be able to superimpose the images from these cameras exactly in order to calculate the polarisation ratio.

As a variant the emitter is a lamp which emits a beam of pulsed strong white light such as for example a xenon lamp pulsed at a frequency which is synchronised with the camera's exposure time, such as for example a frequency of 15 Hz.

Advantageously, use of such a lamp makes it possible to use a camera of low sensitivity and therefore low cost.

The invention claimed is:

1. A device for evaluating a state of wetting of a surface, the device comprising:
   at least one emitter able to emit at least one light beam which is incident in a direction of a surface, the surface being able to at least partly reflect the beam;
   a single means for receiving the beam reflected by the surface;
   means for polarisation comprising at least one first polarisation zone and one second polarisation zone capable of polarising a first part and a second part of the beam in a first polarisation direction and a second polarisation direction respectively, the first part and the second part of the beam having a first wavelength and a second wavelength respectively, the second wavelength being different from the first wavelength, and the means for polarisation being located between the emitter and the surface under analysis;
   means for recombining the first part and the second part of the polarized beam in the first polarisation direction and the second polarisation direction respectively in only one beam, the means for recombination being located between the emitter and the surface; and
   means for calculation capable of calculating a polarisation ratio between the polarisations of the first part of the reflected beam and the second part of the reflected beam in order to evaluate the state of wetting of the surface.

2. The evaluation device according to claim 1, wherein the first polarisation zone is capable of polarising only the first part of the beam and the second polarisation zone is capable of polarising only the second part of the beam.

3. The evaluation device according to claim 1, wherein the first polarisation direction is substantially perpendicular to the second polarisation direction.

4. The evaluation device according to claim 1, wherein a means for receiving comprise means for creating an image in colour, the image comprising pixels of a first colour capable of being excited by the first part of the beam and pixels of a second colour capable of being excited by the second part of the beam, and a polarisation ratio is calculated from a mean of grey levels of the pixels of the first colour and a mean of grey levels of the pixels of the second colour.

5. A method for evaluating a state of wetting of a surface capable of reflecting at least a part of an incident light beam, comprising:
   emitting at least one incident beam in a direction of the surface by an emitter,
   polarising at least a first part and a second part of the beam in a first polarisation direction and a second polarisation direction by at least a first polarisation zone and a second polarisation zone respectively, the first part and the second part of the beam having a first wavelength and a second wavelength respectively, the second wavelength being different from the first wavelength, with means for polarisation being located between the emitter and the surface;
   recombining the first part and the second part of the polarized beam in the first polarisation direction and the second polarisation direction respectively in only one beam, a means for recombining being located between the emitter and the surface;
   receiving the first part and the second part of the beam polarised by the receiving means; and
   evaluating the state of wetting of the surface by calculating a polarisation ratio between the polarisation of the first part of the reflected by beam and the second part of the reflected beam by means for calculation.

6. The method of evaluation according to claim 5, wherein the receiving stage comprises a stage of creating an image representing the first part and the second part of the polarised beam, and the evaluation stage comprises the following stages:
   determining a wetting density of the surface by calculating a degree of saturation of the image;
   comparing the wetting density with at least one predetermined primary wetting density threshold;
   if the wetting density is below the primary wetting density threshold, comparing the polarisation ratio with a predetermined polarisation threshold; and
   classifying the surface as a dry surface when a polarisation coefficient is above the polarisation threshold and as a wet surface when the polarisation coefficient is below the polarisation threshold 7. The method of evaluation according to claim 6, wherein the evaluation stage further comprises the following stages:
   if the wetting density is above the primary wetting density threshold, comparing the wetting density with at least one secondary wetting density threshold; and
   classifying the surface as a slightly wetted surface when the wetting density is below the secondary wetting density threshold and as a heavily wetted surface when the wetting density is above the secondary wetting density threshold.

8. A device for indicating a state of wetting of a road for a motor vehicle travelling on that road, the vehicle incorporating means for emission/receiving, comprising:
   means for control comprising:
      means for connection to the vehicle's emission/receiving means to transmit a request for characterisation of a road type to a remote server and to receive the type,
      a mapping defining polarisation threshold values, of primary wetting density thresholds and secondary wetting density thresholds on a basis of different road types,
      means for selecting at least one of the said values from the mapping according to the road type received by the means for emission/receiving, and
      means for transmitting the selected value or each selected value to an evaluation device;
   the device for evaluating the state of wetting according to claim 1, the device including a predetermined polarisation threshold a predetermined primary wetting density threshold and a predetermined secondary wetting density threshold, the device being capable of receiving the value or each value selected by the means for control, and of modifying
   a predetermined value or each predetermined value by the value or each value received.

9. A device for evaluating a state of wetting of a surface, the device comprising:
   at least one emitter able to emit at least one light beam which is incident in a direction of a surface, the surface being able to at least partly reflect the beam;
   a single receiver configured to receive the beam reflected by the surface;
   a polariser comprising at least one first polarisation zone and one second polarisation zone capable of polarising a first part and a second part of the beam in a first polarisation direction and a second polarisation direction respectively, the first part and the second part of the beam having a first wavelength and a second wavelength respectively, the second wavelength being different from the first wavelength, and the polariser being located between the emitter and the surface under analysis;
   a recombiner of the first part and the second part of the polarized beam in the first polarisation direction and the second polarisation direction respectively in only one beam, the recombiner being located between the emitter and the surface; and
   a calculator configured for calculating a polarisation ratio between the polarisations of the first part of the reflected beam and the second part of the reflected beam in order to evaluate the state of wetting of the surface.

10. The evaluation device according to claim 9, wherein the first polarisation zone is capable of polarising only the first part of the beam and the second polarisation zone is capable of polarising only the second part of the beam.

11. The evaluation device according to claim 9, wherein the first polarisation direction is substantially perpendicular to the second polarisation direction.

12. The evaluation device according to claim 9, wherein a receiver is configured for creating an image in colour, the image comprising pixels of a first colour capable of being excited by the first part of the beam and pixels of a second colour capable of being excited by the second part of the beam, and a polarisation ratio is calculated from a mean of grey levels of the pixels of the first colour and a mean of grey levels of the pixels of the second colour.

* * * * *